United States Patent [19]
Wang et al.

[11] Patent Number: 6,075,044
[45] Date of Patent: Jun. 13, 2000

[54] HETEROCYCLIC DERIVATIVES AS INHIBITORS OF PURINE SALVAGE PHOSPHORIBOSYLTRANSFERASES

[75] Inventors: Ching C. Wang; John Somoza; Jon P. Page, all of San Francisco, Calif.; Ronaldus Marcellus Alphonsus Knegtel, Nbijmegen, Netherlands; Irwin D. Kuntz, Greenbrae, Calif.; Connie M. Oshiro, Mountain View, Calif.; A. Geoffrey Skillman, San Francisco, Calif.

[73] Assignee: The Regents of the University of California, San Francisco, Calif.

[21] Appl. No.: 09/118,451

[22] Filed: Jul. 17, 1998

Related U.S. Application Data

[60] Provisional application No. 60/053,296, Jul. 21, 1997, and provisional application No. 60/053,297, Jul. 21, 1997.

[51] Int. Cl.[7] .................................................. A01N 43/38

[52] U.S. Cl. .......................... 514/415; 514/416; 514/417; 514/418; 514/421; 514/443; 514/469; 514/470; 514/471; 514/472; 514/473; 514/510; 514/561; 514/567; 514/569; 514/614; 514/615; 514/617; 514/619; 514/639; 514/641; 514/644; 514/646; 514/657; 514/672; 514/681; 514/684; 514/706; 514/708; 514/709; 514/717; 514/727; 514/729; 514/730; 514/732; 514/741; 514/742; 514/765; 514/570; 514/571

[58] Field of Search ..................................... 514/415, 570, 514/416, 571, 417, 418, 421, 470, 443, 469, 471, 472, 473, 510, 561, 567, 569, 614, 615, 617, 619, 639, 641, 644, 646, 657, 672, 681, 684, 706, 708, 709, 717, 727, 729, 730, 732, 741, 742, 765

[56] References Cited

PUBLICATIONS

Aldritt, Susan M. and Wang, Ching C., "Purification and Characterization of Guanine Phosphoribosyltransferase from *Giardia lamblia*", *J. Biol. Chem.*, vol. 261, pp. 8528–8533 (1986).

Beck, Joanne T. and Wang, C.C., "The Hypoxanthine–Guanine–Xanthine Phosphoribosyltransfease from *Tritrichomonas foetus* has Unique Properties", *Mol. Biochem. Parasitol.*, vol. 60, pp. 187–194 (1993).

Chin, Marian S. and Wang, Ching C., "Isolation, Sequencing and Expression of the Gene Encoding Hypoxanthine–Guanine–Xanthine Phosphoribosyltransferase of *Tritrichomonas foetus*", *Mol. Biochem. Parasitol.*, vol. 63, pp. 221–230 (1994).

Sommer, et al., "Cloning, Expression and Characterization of an Unusual Guanine Phosphoribosyltransferase from *Giardia lamblia*", *Mol. Biochem. Parasitol*, vol. 78, pp. 185–193 (1996).

Somoza, et al., "Crystal Structure of the Hypoxanthine–Guanine–Xanthine Phosphoribosyltransferase from the Protozoan Parasite *Tritrichomonas foetus*", *Biochemistry*, vol. 35, pp7032–7040 (1996).

Somoza, et al., "Rational Design of Novel Antimicrobials: Blocking Purine Salvage in a Parasitic Protozoan", *Biochemistry*, vol. 37, pp. 5344–5348 (1998).

Wang, C.C., "Current Problems in Anti–Parasite Chemotherapy", *Trends Biochem. Sci.*, vol. 7, pp. 354–356 (1982).

Wang, C.C., et al., "Purine Salvage by *Tritrichomonas Foetus*", *Mol. Biochem. Parasitol.*, vol. 8, pp 325–337, 1987.

*Primary Examiner*—Frederick Krass
*Attorney, Agent, or Firm*—Cooley Godward LLP

[57] ABSTRACT

The use of certain heterocyclic derivatives for treating parasitic protozoa infections in mammals, in particular bovine trichomoniasis and giardiasis, is disclosed.

25 Claims, No Drawings

HETEROCYCLIC DERIVATIVES AS INHIBITORS OF PURINE SALVAGE PHOSPHORIBOSYLTRANSFERASES

CROSS REFERENCE TO RELATED APPLICATION

This application claims the benefit of U.S. Provisional Application Ser. Nos. 60/053,296 and 60/053,297, both of which were filed on Jul. 21, 1997.

This invention was made with Government support under Grant No. AI19391, awarded by the National Institute of Health. The Government has certain rights in this invention.

BACKGROUND OF THE INVENTION

1. Field of the Invention

This invention pertains to heterocyclic derivatives that are useful for treating parasitic protozoa infections in mammals, in particular bovine trichomoniasis and giardiasis.

2. Related Disclosures

Parasitic protozoa infections in mammals are widespread and difficult to prevent or remedy effectively. For example, *Tritrichomonas foetus* is an anaerobic protozoan parasite that causes bovine trichomoniasis in cattle; it is prevalent in cattle herds throughout much of the world, and causes a substantial loss in beef production. *Gardia lamblia* is an example of a water-borne zoonotic protozoan parasite; it is also found worldwide, and infection leads to severe diarrhea and growth retardation in humans.

It has been observed that parasitic protozoa lack a de novo purine nucleotide synthetic pathway (Wang, *Trends Biochem. Sci.* 7:354–356 (1982)). For example, *T. foetus* relies upon possession of hypoxanthine-guanine-xanthine phosphoribosyltransferase enzyme (HGXPRTase) in order to salvage purine bases from the host. Similarly, *G. lamblia* relies upon guanine phosphoribosyltransferase enzyme (GPRTase) for supplying its guanine nucleotide pool.

It is apparent that inhibition of the purine salvage pathways of the parasitic protozoa would be an effective way to block the ability of the parasites to survive in the host. However, it is important that any compounds capable of such an inhibiting effect should not interfere with the host HGPRTase. For example, in humans defects in HGPRTase are known to be responsible for gouty arthritis and a number of central nervous system disorders.

To assist in the identification of compounds that selectively inhibit purine salvage pathways, both enzymes (HGXPRTase from *T. foetus* and GPRTase from *G. lamblia*) were purified to homogeneity and partially characterized (Beck, et al., *Mol. Biochem. Parasitol.* 60:187–194 (1993); Aldritt, et al., *J. Biol. Chem.* 261:8528–8533 (1986)). The genes encoding the two enzymes were cloned, sequenced and expressed in transformed Escherichia coli to produce large quantities of recombinant enzyme proteins in their native state (Chin, et al., *Mol. Biochem. Parasitol.* 63:221–230 (1994); Sommer, et al., *Mol. Biochem. Parasitol.* 78:185–193 (1996)). The purified recombinant *T. foetus* HGXPRTase was crystallized and the crystal structure was determined by X-ray crystallography in the laboratory of Professor Robert Fletterick of the Department of Biochemistry and Biophysics at UCSF (Somoza, et al., *Biochemistry* 35:7032–7040 (1996)). Computer modeling of the active site in the enzyme molecule was initiated in the laboratory of Professor Irwin Kuntz to identify chemical compounds that conform to the dimensions of (and complement the chemistry of) the pocket and thus inhibit the enzyme function. A group of heterocyclic compounds have been found that conform to the dimensions of the pocket and complement its chemistry, and inhibit the purine salvage pathways of the parasites without affecting the mammalian HGPRTase.

SUMMARY OF THE INVENTION

One aspect of the invention is related to a method of treating parasitic protozoa infections in mammals, which method comprises administering to a mammal in need of such a treatment a therapeutically effective amount of a compound of Formula I:

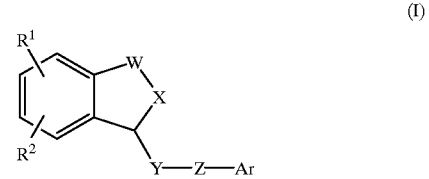

(I)

wherein:

$R^1$ and $R^2$ are independently chosen from a group consisting of hydrogen, lower alkyl, lower alkoxy, hydroxy, trifluoromethyl, halo, nitro, —$NR^3R^4$, —N(CO)$R^3$, and —C(O)$NR^3R^4$;

W is —C($R^3$)($R^4$)—, —NH—, —O—, or —S(O)$_n$—;

X is C=O, C=S, or CH(OH);

Y is =N—$NR^3$—, =N—N=C($R^3$)—, =N—N=, —N($R^3$)—N($R^4$)—, =C($R^3$)—, or =C—$NR^3$—; and Z is —[C(O)]$_m$—(C$R^3R^4$)$_n$—(O)$_p$—;

in which:

$R^3$ and $R^4$ at every occurrence are independently hydrogen or lower alkyl;

m is 1 or 1;

n is 0, 1, 2, 3, or 4;

p is 0 or 1; and

Ar is aryl or heteroaryl;

and the pharmaceutically acceptable salts thereof.

In a second aspect, the invention relates to a pharmaceutical composition containing a therapeutically effective amount of a compound of Formula I admixed with one or more pharmaceutically acceptable excipients.

A third aspect of the invention is related to a method of treating parasitic protozoa infections in mammals, which method comprises administering to a mammal in need of such a treatment a therapeutically effective amount of a compound of Formula II:

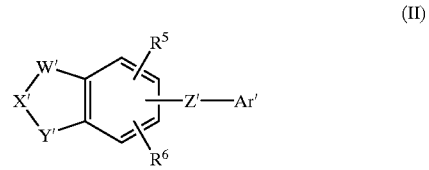

(II)

wherein:

$R^5$ and $R^6$ are independently chosen from a group consisting of hydrogen, alkyl, alkoxy, hydroxy, trifluoromethyl, halogen, nitro, —$NR^7R^8$, —N(CO)$R^7$, and —C(O)$NR^7R^8$;

W' is C=O, C=S, C=$NR^7$, C$R^7R^8$, or C($R^7$)OH;

X' is —O—, —NR$^7$—, —S(O)$_r$, or —CR$^7$R$^8$;

Y' is —V—R$^9$— or —R$^9$—V—;

in which:

R$^9$ is —CR$^7$R$^8$— or a covalent bond; and

V is C=O, C=S, C=NR$^7$, CR$^7$R$^8$, or C(R$^7$)OH;

Z' is —C(T)NR$^7$—, —NR$^7$C(T)—, —NR$^7$C(T)NR$^8$—, —N=N—, —(R$^7$R$^8$)$_q$—, —CR$^7$=CR$^8$—, —S(O)$_r$R$^7$R$^8$—, or —OR$^7$R$^8$—;

in which:

q is 1,2,or 3;

r is 0, 1, or 2;

T is O, S, or =NR$^7$; and

R$^7$ and R$^8$ are independently hydrogen or lower alkyl; and

Ar' is aryl or heteroaryl; and the pharmaceutically acceptable salts thereof.

In a fourth aspect, the invention relates to a pharmaceutical composition containing a therapeutically effective amount of a compound of Formula II admixed with one or more pharmaceutically acceptable excipients.

DETAILED DESCRIPTION OF THE INVENTION

Definitions

As used herein:

"Alkyl" means a branched or unbranched saturated monovalent hydrocarbon radical containing 1 to 8 carbon atoms, such as methyl, ethyl, propyl, tert-butyl, n-hexyl, n-octyl and the like.

"Lower alkyl" means a branched or unbranched saturated monovalent hydrocarbon radical containing 1 to 6 carbon atoms, such as methyl, ethyl, propyl, isopropyl, tert-butyl, butyl, n-hexyl and the like, unless otherwise indicated.

"Lower alkoxy" means the group —O-(lower alkyl) wherein lower alkyl is as herein defined.

"Halo" or means fluoro, chloro, bromo, or iodo.

The term "aryl" refers to a monovalent unsaturated aromatic carbocyclic radical having a single ring (e.g., phenyl) or two rings (e.g., naphthyl or biphenyl), which can optionally be mono-, di- or tri-substituted, independently, with OH, COOH, lower alkyl, lower alkoxy, halo, nitro, amino, alkylamino, dialkylamino, trifluoromethyl and/or cyano.

The term "heteroaryl" refers to a monovalent aromatic carbocyclic radical having 1–3 heteroatoms within a single ring, (e.g., such as pyridyl, imidazolyl, thiazolyl, pyrimidine, oxazolyl, and the like), or within two rings (e.g., indolyl, quinolinyl, benzofuranyl, and the like) which can optionally be mono-, di- or tri-substituted, independently, with OH, COOH, lower alkyl, lower alkoxy, halo, nitro, amino, alkylamino, dialkylamino, trifluoromethyl and/or cyano.

The term "heteroatom" refers to oxygen, sulfur and nitrogen, unless otherwise specified.

The term "q.s" is used herein to mean adding a quantity sufficient to achieve a stated function., for example to bring a solution to a desired volume (q.s. to 100 ml) or to a desired pH (q.s. to pH 4).

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl.

It should be understood that Formulas I and II as drawn are intended to represent the racemic form of compounds of Formulas I and II as well as the individual enantiomers and non-racemic mixtures thereof. The scope of the invention as described and claimed encompasses the racemic forms of the compounds of Formulas I and II as well as the individual enantiomers and non-racemic mixtures thereof.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e. arresting its development; or (iii) relieving the disease, i.e. causing regression of the disease.

The term "disease state which is alleviated by treatment with an inhibitor of the purine salvage pathways of parasitic protozoa" as used herein is intended to cover all disease states which are generally acknowledged in the art to be usefully treated with inhibitors of the purine salvage pathways of parasitic protozoa in general, and those disease states which have been found to be usefully treated by the specific compounds of our invention, the compounds of Formula I.

The term "therapeutically effective amount" refers to that amount which is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art.

One example of a compound of Formula I is illustrated below in order to demonstrate the numbering system used in the nomenclature for describing such compounds:

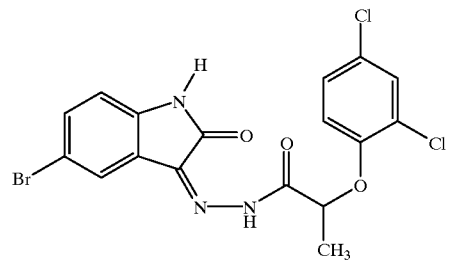

This is a compound of Formula I where R$^1$ is 5-bromo; R$^2$ is hydrogen; W is —NH—; X is —C=O; Y is =N—NR$^3$, in which R$^3$ is hydrogen; Z is —[C(O)]$_m$—(CR$^3$R$^4$)$_n$—(O)$_p$—, in which m, n and p are all 1, R$^3$ is hydrogen, R$^4$ is methyl; and Ar is 2,4-dichlorophenyl. This compound is named 3-(2,4-dichlorophenoxy)-2-propylcarbazoyl-5-bromoindol-2,3-dione. This compound is also referred to as 3-[2-(2,4-dichlorophenoxy)propanoylhydrazono]-5-bromo-1,3-dihydroindol-2-one.

One example of a compound of Formula II is illustrated below in order to demonstrate the numbering system used in the nomenclature for describing such compounds:

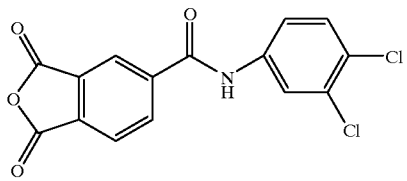

This is a compound of Formula II where $R^5$ and $R^6$ are hydrogen; W' is —C=O; X' is —O—; Y' is —C=O; Z' is —C(T)NR$^7$—, in which T is O, and $R^7$ is hydrogen; and Ar' is 3,4-dichlorophenyl. This compound is named: 5-[N-(3,4-dichlorophenyl)carbamoyl]-1,3-isobenzofurandione.

METHODS OF PREPARATION

The compounds of Formulas I and II are either commercially available, for example from Menai, Sigma Chemicals, Maybridge Chemicals, or alternatively may be prepared by means well known in the art.

UTILITY AND ADMINISTRATION

General Utility

The compounds of Formulas I and II and the pharmaceutically acceptable salts thereof have been found to possess valuable pharmacological properties, and have been shown to be useful as selective inhibitors of the purine salvage pathways of parasitic protozoa. Accordingly these compounds and pharmaceutically acceptable compositions containing them are useful for treating parasitic protozoa infections, and in particular are useful for the treatment of trichomoniasis and giardiasis.

Testing

The potential of the compounds for utility against parasitic protozoa infections, in particular *Tritrichomonas foetus* and *Giardia lamblia*, is determined by the method, described in Example 1, of Wang, et al., *Mol. Biochem. Parasitol.* 8:325–337 (1983).

General Administration

In applying the compounds of this invention to treatment of the above conditions, administration of the active compounds and salts described herein can be via any of the accepted modes of administration, including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of Formula I or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 0.1–50 mg/kg/day, preferably 1–20 mg/kg/day. For an average 70 kg human, this would amount to 7 to 3500 mg per day, or preferably 70 to 1400 mg/day.

For solid compositions, conventional non-toxic solid carriers include, for example, pharmaceutical grades of mannitol, lactose, starch, magnesium stearate, sodium saccharin, talcum, cellulose, sodium crosscarmellose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition or formulation to be administered will, in any event, contain a quantity of the active compound(s) in an amount effective to alleviate the symptoms of the subject being treated.

Dosage forms or compositions containing active ingredient (compounds of Formulas I and II or their salts) in the range of 0.025 to 95 wt % with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, sodium crosscarmellose, glucose, sucrose, magnesium, carbonate, and the like. Such compositions take the form of solutions, suspensions, tablets, capsules, powders, sustained release formulations and the like. Such compositions may contain 0.1–95 wt % active ingredient, preferably 0.5–80 wt %.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is hereby incorporated by reference.

The percentage of active compound contained in such parental compositions is highly dependent on the specific nature thereof, as well as the activity of the compound and the needs of the subject. However, percentages of active ingredient of 0.01 wt % to 10 wt % in solution are employable, and will be higher if the composition is a solid which will be subsequently diluted to the above percentages. Preferably the composition will comprise 0.02–8 wt % of the active agent in solution.

For systemic administration via suppository, traditional binders and carriers include, e.g. polyalkylene glycols or triglycerides. Such suppositories may be formed from mixtures containing active ingredient in the range of 0.05–10 wt %; preferably 0.1–2 wt %.

In applying the compounds of the invention to treatment of diseases or disorders of the eye which are associated with an abnormally high intraocular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.001 wt % to 10 wt %, most preferably 0.005 wt % to 1 wt % of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6–8. Typical sterilants are phenyl mercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8–8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, a typical ocular composition could be administered at the rate of about 2–10 drops per day per eye of a 0.1 wt % solution of active ingredient.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc.

If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see *Remington's Pharmaceutical Sciences*, Mack Publishing Company, Easton, Pa., 16th Edition, 1980.

The following preparations and examples illustrate the invention but are not intended to limit its scope.

EXAMPLE 1

Protocol For Testing Compounds of Formula I Against *Tritrichomonas foetus* HGXPRTase, *Giardia lamblia* GPRTase and Human HGPRTase The enzyme assay mixture, in a final volume of 20 $\mu$l, consisted of the following:

| | |
|---|---|
| Bis-Tris-HCl, pH 6.8 | 0.3 M |
| MgCl$_2$ | 12 mM |
| 5-Phospho-1-ribosylpyrophosphate | 0.1 mM |
| [$^{14}$C]-guanine (46 mCi/mmole) | 22 $\mu$M |

The chemical compound to be tested was dissolved in dimethyl sulfoxide (DMSO) to a concentration 10-fold higher than that to be tested and diluted 10-fold in the assay mixture. Thus, all the assay mixtures contain 10% DMSO.

The recombinant enzyme, purified to homogeneity in the native form, was diluted in a buffer solution of 50 mM Bis-Tris-HCl, pH 6.8, 6 mM MgCl$_2$, and 1 mM dithiothreitol to a final concentration of 34 $\mu$g enzyme protein per ml. Two and one half of the diluted enzyme solution was added to the 20 $\mu$l reaction mixture, and maintained at 37° C., to start the enzyme-catalyzed reaction. The reaction was allowed to proceed at 37° C. for exactly 5 min, and then stopped by adding 23 $\mu$l of 1 mM guanine and 1 mM GMP to the reaction mixture.

Twenty $\mu$l of the final mixture was spotted on a polyethyleneimine-cellulose thin layer plate and chromatographed with 5 mM ammonium acetate pH 5.0. The unreacted [$^{14}$C]-guanine migrated at the forefront of the chromatography with an R$_f$ value of 0.62, whereas the product [$^{14}$C]-GMP remained at the origin due to the negative charge of the molecule at pH 5.0. The spots of guanine and GMP were cut out from the plate, and the radioactivity in each spot measured with a Beckman LS-3801 scintillation counter. The radioactivities associated with the GMP and diminished from the guanine sample were used to calculate the amount of substrate converted to product within a unit time period.

TABLE 1

Compounds of Formula I Tested

| Compound | R$^1$ | Y | m | n | p | Ar |
|---|---|---|---|---|---|---|
| (I)1 | H | =N—NH— | 0 | 0 | 0 | 4-nitrophenyl |
| (I)2 | H | =N—N=CH— | 0 | 0 | 0 | 4-nitrophenyl |
| (I)3 | H | =N—N=CH— | 0 | 0 | 0 | 4-chlorophenyl |
| (I)4 | H | =N—N=CH— | 0 | 0 | 0 | 2-hydroxy-3,5-dichlorophenyl |
| (I)5 | H | =N—N=CH— | 0 | 0 | 0 | 2-hydroxy-5-bromophenyl |
| (I)6 | Br | =N—N=CH— | 0 | 0 | 0 | 3,4-dichloro-phenyl |
| (I)7 | H | =C—NH— | 0 | 2 R$^3$=R$^4$=H | 0 | 4-methoxy-phenyl |

TABLE 1-continued

Compounds of Formula I Tested

| Compound | $R^1$ | Y | m | n | p | Ar |
|---|---|---|---|---|---|---|
| (I)8 | H | =N—NH— | 1 | 1<br>$R^3=R^4=H$ | 1 | 4-nitrophenyl |
| (I)9 | Br | =N—NH— | 1 | 1<br>$R^3=H$<br>$R^4=CH_3$ | 1 | 2,4-dichlorophenyl |
| (I)10 | H | =N—NH— | 1 | 1<br>$R^3=R^4=H$ | 0 | 3,4-dimethoxy-phenyl |

In compounds (I)1–(I)10, $R^2$ is hydrogen, W is —NH—, and X is —C=O.

The compounds are named as follows:

(I)1  3-(4-nitrophenylhydrazono)-1,3-dihydroindol-2-one.
(I)2  3-(4-nitrophenylidenehydrazono)-1,3-dihydroindol-2-one.
(I)3  3-(4-chlorophenylidenehydrazono)-1,3-dihydroindol-2-one.
(I)4  3-(2-hydroxy-3,5-dichlorophenylidenehydrazono)-1,3-dihydroindol-2-one.
(I)5  3-(2-hydroxy-5-bromophenylidenehydrazono)-1,3-dihydroindol-2-one.
(I)6  3-(3,4-dichlorophenylidenehydrazono)-5-bromo-1,3-dihydroindol-2-one.
(I)7  3-[(3-(4-methoxyphenethylamino)methylene]-1,3-dihydroindol-2-one.
(I)8  3-(4-nitrophenoxy)acetylhydrazono]-1,3-dihydroindol-2-one.
(I)9  3-[2-(2,4-dichlorophenoxy)propanoylhydrazono]-5-bromo-1,3-dihydroindol-2-one.
(I)10  3-[(3,4-dimethoxyphenyl)acetylhydrazono]-5-bromo-1,3-dihydroindol-2-one.

TABLE 2

Results of Testing, $IC_{50}(\mu M)$

| Compound | TFH | GLG | HH |
|---|---|---|---|
| (I)1 | 240 | >1000 | 200 |
| (I)2 | 50 | >1000 | >1000 |
| (I)3 | 170 | >1000 | >1000 |
| (I)4 | >1000 | >1000 | ND |
| (I)5 | 460 | >1000 | >1000 |
| (I)6 | 300 | >1000 | >1000 |
| (I)7 | 200 | >1000 | >1000 |
| (I)8 | 180 | >1000 | >1000 |
| (I)9 | 85 | 30 | >1000 |
| (I)10 | 320 | 90 | >1000 | where:

"TFH" is HGXPRTase from *T. foetus;*
"GLG" is GPRTase from *G. lamblia*; and
"HH" is Human HGPRTase.

EXAMPLE 2

Protocol For Testing Compounds of Formula II Against *Tritrichomonas foetus* HGXPRTase *Giardia lamblia* GPRTase and Human HGPRTase The enzyme assay mixture, in a final volume of 20 $\mu$l, consisted of the following:

| Bis-Tris-HCl, pH 6.8 | 0.3 M |
|---|---|
| $MgCl_2$ | 12 mM |
| 5-Phospho-1-ribosylpyrophosphate | 0.1 mM |
| [$^{14}$C]-guanine (46 mCi/mmole) | 22 $\mu$M |

The chemical compound to be tested was dissolved in dimethyl sulfoxide (DMSO) to a concentration 10-fold higher than that to be tested and diluted 10-fold in the assay mixture. Thus, all the assay mixtures contain 10% DMSO.

The recombinant enzyme, purified to homogeneity in the native form, was diluted in a buffer solution of 50 mM Bis-Tris-HCl, pH 6.8, 6 mM $MgCl_2$, and 1 mM dithiothreitol to a final concentration of 34 $\mu$g enzyme protein per ml. Two and one half $\mu$l of the diluted enzyme solution was added to the 20 $\mu$l reaction mixture, and maintained at 37° C., to start the enzyme-catalyzed reaction. The reaction was allowed to proceed at 37° C. for exactly 5 min, and then stopped by adding 23 $\mu$l of 1 mM guanine and 1 mM GMP to the reaction mixture.

Twenty $\mu$l of the final mixture was spotted on a polyethyleneimine-cellulose thin layer plate and chromatographed with 5 mM ammonium acetate pH 5.0. The unreacted [$^{14}$C]-guanine migrated at the forefront of the chromatography with an $R_f$ value of 0.62, whereas the product [$^{14}$C]-GMP remained at the origin due to the negative charge of the molecule at pH 5.0. The spots of guanine and GMP were cut out from the plate, and the radioactivity in each spot measured with a Beckman LS-3801 scintillation counter. The radioactivities associated with the GMP and diminished from the guanine sample were used to calculate the amount of substrate converted to product within a unit time period.

TABLE 3

Compounds of Formula II Tested

| Compound | $R^5$ | X' | Y' | Z' | Ar' |
|---|---|---|---|---|---|
| (II)1 | H | 0 | C=O | —C(O)NH— | 3-nitrophenyl |
| (II)2 | H | 0 | C=O | —C(O)NH— | 4-acetamidophenyl |

TABLE 3-continued

Compounds of Formula II Tested

| Compound | $R^5$ | X' | Y' | Z' | Ar' |
|---|---|---|---|---|---|
| (II)3 | H | 0 | C=O | —C(O)NH— | 3,4-dichlorophenyl |
| (II)4 | H | 0 | C=O | —C(O)NH— | 2-methoxy-5-nitrophenyl |
| (II)5 | H | 0 | C=O | —C(O)NH— | 2,4-dichlorophenyl |
| (II)6 | H | 0 | C=O | —C(O)NH— | 2-methoxy-5-chlorophenyl |
| (II)7 | H | 0 | $CH_2$ | —NHC(O)— | 4-chlorophenyl |
| (II)8 | —$NO_2$— | —N(H)— | C=O | —$SCH_2$— | 4-chlorophenyl |

In compounds (II)1–(II)8, $R^6$ is hydrogen, W' is C=O, and —Z'—Ar' is in the 5-position.

The compounds are named as follows:

(II)1  5-[N-(3-nitrophenyl)carbamoyl]-1,3-isobenzofurandione;
(II)2  5-[N-(4-acetamidophenyl)carbamoyl]-1,3-isobenzofurandione;
(II)3  5-[N-(3,4-dichlorophenyl)carbamoyl]-1,3-isobenzofurandione;
(II)4  5-[N-(2-methoxy-5-nitrophenyl)carbamoyl]-1,3-isobenzofurandione;
(II)5  5-[N-(2,4-dichlorophenyl)carbamoyl]-1,3-isobenzofurandione;
(II)6  5-[N-(2-methoxy-5-chlorophenyl)carbamoyl]-1,3-isobenzofurandione;
(II)7  5-[N-(4-chlorophenyl)carbonylamino]-3-isobenzofuranone;
(II)8  5-[N-(4-chlorophenyl)methylthio]-6-nitrophthalimide.

TABLE 4

Results of Testing, $IC_{50}(\mu M)$

| Compound | TFH | GLG | HH |
|---|---|---|---|
| (II)1 | 300 | >1000 | >1000 |
| (II)2 | 140 | >1000 | >1000 |
| (II)3 | 50 | 30 | >1000 |
| (II)4 | 70 | 500 | >1000 |
| (II)5 | 80 | 200 | >1000 |
| (II)6 | 22 | 750 | >1000 |
| (II)7 | 380 | >1000 | >1000 |
| (II)8 | 425 | >1000 | >1000 | where:
"TFH" is HGXPRTase from *T. foetus*;
"GLG" is GPRTase from *G. lamblia*; and
"HH" is Human HGPRTase.

EXAMPLE 3

This example illustrates the preparation of a representative pharmaceutical formulation for oral administration containing an active compound of Formula I, e.g. 3-(2,4-dichlorophenoxy)-2-propylcarbazoyl-5-bromoindol-2,3-dione.

| Ingredients | Quantity per tablet, mg |
|---|---|
| Active Compound | 200 |
| Lactose, spray-dried | 148 |
| Magnesium stearate | 2 |

The above ingredients are mixed and introduced into a hard-shell gelatin capsule.

Other compounds of Formula I can be used as the active compound in the preparation of the orally administrable formulations of this example.

EXAMPLE 4

This example illustrates the preparation of a representative pharmaceutical formulation for oral administration containing an active compound of Formula II, e.g. 5-[N-(3,4-dichlorophenyl)carbamoyl]-1,3-isobenzofurandione.

| Ingredients | Quantity per tablet, mg |
|---|---|
| Active Compound | 200 |
| Lactose, spray-dried | 148 |
| Magnesium stearate | 2 |

The above ingredients are mixed and introduced into a hard-shell gelatin capsule.

Other compounds of Formula II can be used as the active compound in the preparation of the orally administrable formulations of this example.

EXAMPLE 5

This example illustrates the preparation of another representative pharmaceutical formulation for oral administration containing an active compound of Formula I, e.g., 3-(2,4-dichlorophenoxy)-2-propylcarbazoyl-5-bromoindol-2,3-dione.

| Ingredients | Quantity per tablet, mg |
|---|---|
| Active Compound | 400 |
| Cornstarch | 50 |
| Lactose | 145 |
| Magnesium stearate | 5 |

The above ingredients are mixed intimately and pressed into single scored tablets.

Other compounds of Formula I can be used as the active compound in the preparation of the orally administrable formulations of this example.

EXAMPLE 6

This example illustrates the preparation of another representative pharmaceutical formulation for oral administration containing an active compound of Formula II, e.g., 5-[N-(3,4-dichlorophenyl)carbamoyl]-1,3-isobenzofurandione.

| Ingredients | Quantity per tablet, mg |
| --- | --- |
| Active Compound | 400 |
| Cornstarch | 50 |
| Lactose | 145 |
| Magnesium stearate | 5 |

The above ingredients are mixed intimately and pressed into single scored tablets.

Other compounds of Formula II can be used as the active compound in the preparation of the orally administrable formulations of this example.

EXAMPLE 7

This example illustrates the preparation of a representative pharmaceutical formulation containing an active compound of Formula I, e.g., 3-(2,4-dichlorophenoxy)-2-propylcarbazoyl-5-bromoindol-2,3-dione. An oral suspension is prepared having the following composition.

| Ingredients | Amount |
| --- | --- |
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol(70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other compounds of Formula I can be used as the active compound in the preparation of the orally administrable formulations of this example.

EXAMPLE 8

This example illustrates the preparation of a representative pharmaceutical formulation containing an active compound of Formula II, e.g., 5-[N-(3,4-dichlorophenyl)carbamoyl]-1,3-isobenzofurandione. An oral suspension is prepared having the following composition.

| Ingredients | Amount |
| --- | --- |
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol(70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other compounds of Formula II can be used as the active compound in the preparation of the orally administrable formulations of this example.

EXAMPLE 9

This example illustrates the preparation of a representative pharmaceutical formulation for oral administration containing an active compound of Formula I, e.g. 3-(2,4-dichlorophenoxy)-2-propylcarbazoyl-5-bromoindol-2,3-dione. An injectable preparation buffered to a pH of 4 is prepared having the following composition:

| Ingredients | Amount |
| --- | --- |
| Active Compound | 0.2 g |
| Sodium Acetate Buffer Solution (0.4 M) | 2.0 ml |
| HCl (1N) | q.s. to pH 4 |
| Water (distilled, sterile) | q.s. to 20 ml |

Other compounds of Formula I can be used as the active compound in the preparation of the injectable formulations of this example.

EXAMPLE 10

This example illustrates the preparation of a representative pharmaceutical formulation for oral administration containing an active compound of Formula II, e.g. 5-[N-(3,4-dichlorophenyl)carbamoyl]-1,3-isobenzofurandione. An injectable preparation buffered to a pH of 4 is prepared having the following composition:

| Ingredients | Amount |
| --- | --- |
| Active Compound | 0.2 g |
| Sodium Acetate Buffer solution (0.4 M) | 2.0 ml |
| HCl (1N) | q.s. to pH 4 |
| Water (distilled, sterile) | q.s. to 20 ml |

Other compounds of Formula II can be used as the active compound in the preparation of the injectable formulations of this example.

EXAMPLE 11

This example illustrates the preparation of a representative pharmaceutical formulation for topical application containing an active compound of Formula I, e.g., 3-(2,4-dichlorophenoxy)-2-propylcarbazoyl-5-bromoindol-2,3-dione.

| Ingredients | grams |
| --- | --- |
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. to 100 g.

Other compounds of Formula I can be used as the active compound in the preparation of the topical formulations of this example.

EXAMPLE 12

This example illustrates the preparation of a representative pharmaceutical formulation for topical application containing an active compound of Formula II, e.g., 5-[N-(3,4-dichlorophenyl)carbamoyl]-1,3-isobenzofurandione.

| Ingredients | grams |
|---|---|
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. to 100 g.

Other compounds of Formula II can be used as the active compound in the preparation of the topical formulations of this example.

EXAMPLE 13

This example illustrates the preparation of a representative pharmaceutical formulation containing an active compound of Formula I, e.g., 3-(2,4-dichlorophenoxy)-2-propylcarbazoyl-5-bromoindol-2,3-dione. A suppository totaling 2.5 grams is prepared having the following composition:

| Ingredients | Amount |
|---|---|
| Active Compound | 500 mg |
| Witepsol H-15* | balance |

(*triglycerides of saturated vegetable fatty acid; a product of Riches-Nelson, Inc., New York, N.Y.)

Other compounds of Formula I can be used as the active compound in the preparation of the suppository formulations of this example.

EXAMPLE 14

This example illustrates the preparation of a representative pharmaceutical formulation containing an active compound of Formula II, e.g., 5-[N-(3,4-dichlorophenyl)carbamoyl]-1,3-isobenzofurandione. A suppository totaling 2.5 grams is prepared having the following composition:

| Ingredients | Amount |
|---|---|
| Active Compound | 500 mg |
| Witepsol H-15* | balance |

Other compounds of Formula II can be used as the active compound in the preparation of the suppository formulations of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a disease state in mammals that is alleviated by treatment with an inhibitor of hypoxanthine-guanine-xanthine phoshoribosyltransferase or guanine phosphoribosyltransferase in the purine salvage pathways of parasitic protozoa, which method comprises administering to a mammal in need of such treatment a therapeutically effective amount of a compound of Formula I:

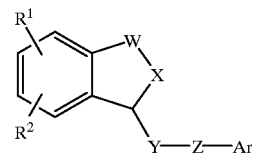

(I)

wherein:
   $R^1$ and $R^2$ are independently chosen from the group consisting of hydrogen, lower alkyl, lower alkoxy, hydroxy, trifluoromethyl, halo, nitro, —$NR^3R^4$, —$N(CO)R^3$, and —$C(O)NR^3R^4$;
   W is —$C(R^3)(R^4)$—, —NH—, —O—, or —$S(O)_n$—;
   X is C=O, C=S, or CH(OH);
   Y is =N—$NR^3$—, =N—N=$C(R^3)$—, =N—N=, —$N(R^3)$—$N(R^4)$—, =$C(R^3)$—, or =C—$NR^3$—; and
   Z is —$(C(O))_m$—$(CR^3R^4)_n$—$(O)_p$—;
in which:
   $R^3$ and $R^4$ at every occurrence are independently hydrogen or lower alkyl;
   m is 0 or 1;
   n is 0, 1, 2, 3, or 4;
   p is 0 or 1; and
   Ar is aryl or heteroaryl;
or a pharmaceutically acceptable salt, ester or N-oxide thereof.

2. The method of claim 1, wherein W is —NH—.

3. The method of claim 2, wherein X is —C=O.

4. The method of claim 3, wherein Y is =N—N=C($R^3$)—.

5. The method of claim 4, wherein $R^3$ is hydrogen, and m, n, and p are all 0.

6. The method of claim 5, wherein Ar is optionally substituted phenyl.

7. The method of claim 6, wherein $R^1$ and $R^2$ are both hydrogen, and Ar is 4-nitrophenyl, namely 3-(4-nitrobenzazido)-indol-2,3-dione.

8. The method of claim 3, wherein Y is =N—$NR^3$—, in which $R^3$ is hydrogen.

9. The method of claim 8, wherein in the Z substituent, $R^3$ is hydrogen, $R^4$ is methyl, and m, n, and p are all 1.

10. The method of claim 9, wherein Ar is optionally substituted phenyl.

11. The method of claim 10, wherein $R^1$ is 5-bromo, $R^2$ is hydrogen, and Ar is 2,4-dichlorophenyl, namely 3-[2-(2,4-dichlorophenoxy)propanoylhydrazono]-5-bromo-1,3-dihydroindol-2-one.

12. The method of claim 1, wherein the disease state is parasitic protozoa infection by bovine trichomoniasis.

13. The method of claim 1, wherein the disease state is parasitic protozoa infection by giardiasis.

14. A method of treating parasitic protozoa infections in mammals, by inhibiting hypoxanthine-guanine-xanthine phosphoribosyltransferase or guanine phosphoribosyltransferase, which method comprises administering to a mammal in need of such treatment a pharmaceutical composition comprising a therapeutically amount of a compound of claim 1 in admixture with at least one pharmaceutically acceptable excipient.

15. A method of treating in mammals a disease state that is alleviated by treatment with an inhibitor of hypoxanthine-guanine-xanthine phosphoribosyltransferase or guanine phosphoribosyltransferase in the purine salvage pathways of parasitic protozoa, which method comprises administering to a mammal in need of such treatment a therapeutically effective amount of a compound of Formula II:

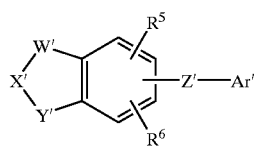

(II)

wherein:

$R^5$ and $R^6$ are independently chosen from the group consisting of hydrogen, alkyl, alkoxy, hydroxy, trifluoromethyl, halogen, nitro, —$NR^7R^8$, —$N(CO)R^7$, and —$C(O)NR^7R^8$;

W' is C=O, C=S, C=$NR^7$, $CR^7R^8$, or $C(R^7)OH$;

X' is —O—, —$NR^7$—, —$S(O)_r$, or —$CR^7R^8$;

Y' is —V—$R^9$— or —$R^9$—V—;

in which:

$R^9$ is —$CR^7R^8$— or a covalent bond; and

V is C=O, C=S, C=$NR^7$, $CR^7R^8$, or $C(R^7)OH$;

Z' is —$C(T)NR^7$—, —$NR^7C(T)$—, —$NR^7C(T)NR^8$—, —N=N—, —$C(R^7R^8)_q$—, —$CR^7$=$CR^8$—, —$S(O)_r$ $R^7R^8$—, or —$OR^7R^8$—;

in which:

q is 1, 2, or 3;

r is 0, 1, or 2;

T is O, S, or =$NR^7$; and $R^7$ and $R^8$ are independently hydrogen or lower alkyl; and Ar' is aryl or heteroaryl;

or the pharmaceutically acceptable salts thereof.

16. The method of claim 15, wherein W' is C=O.

17. The method of claim 16, wherein Y' is —V—$R^9$—, in which V is C=O and $R^9$ is a covalent bond.

18. The method of claim 17, wherein X' is —O—.

19. The method of claim 18, wherein Z' is —C(T)$NR^7$—, in which T is O and $R^7$ is hydrogen.

20. The method of claim 19, wherein $R^5$ and $R^6$ are both hydrogen.

21. The method of claim 20, wherein Ar' is chosen from 3-nitrophenyl, 4-acetamidophenyl, 3,4-dichlorophenyl, 2,4-dichlorophenyl, 2-methoxy-5-nitrophenyl, and 2-methoxy-5-chlorophenyl.

22. The method of claim 20, wherein Ar' is 3,4-dichlorophenyl, namely 5-[N-(3,4-dichlorophenyl)carbamoyl]-1,3-isobenzofurandione.

23. The method of claim 15, wherein the disease state is parasitic protozoa infection by bovine trichomoniasis.

24. The method of claim 15, wherein the disease state is parasitic protozoa infection by giardiasis.

25. A method of treating parasitic protozoa infections in mammals by inhibiting hypoxanthine-guanine-xanthine phosphoribosyltransferase or guanine phosphoribosyltransferase, which method comprises administering to a mammal in need of such treatment a pharmaceutical composition comprising a therapeutically amount of a compound of claim 15 in admixture with at least one pharmaceutically acceptable excipient.

* * * * *